United States Patent [19]

Shmulewitz et al.

[11] Patent Number: 5,833,627
[45] Date of Patent: Nov. 10, 1998

[54] IMAGE-GUIDED BIOPSY APPARATUS AND METHODS OF USE

[75] Inventors: Ascher Shmulewitz; Edo Ziring, both of Mercer Island, Wash.

[73] Assignee: United States Surgical Corporation, Norwalk, Conn.

[21] Appl. No.: 680,595

[22] Filed: Jul. 12, 1996

Related U.S. Application Data

[63] Continuation-in-part of Ser. No. 421,381, Apr. 13, 1995, Pat. No. 5,660,185.

[51] Int. Cl.$^6$ ............................................. A61B 10/00
[52] U.S. Cl. ............................................. 600/562; 128/915
[58] Field of Search ............................. 128/653.1, 662.03, 128/662.05, 749, 754, 915; 606/130, 407, 459, 461, 562, 567

[56] References Cited

U.S. PATENT DOCUMENTS

| | | |
|---|---|---|
| Re. 30,397 | 9/1980 | King . |
| 2,707,662 | 5/1955 | Goldfield et al. . |
| 3,165,630 | 1/1965 | Bielat et al. . |
| 3,420,097 | 1/1969 | Battermann et al. . |

(List continued on next page.)

FOREIGN PATENT DOCUMENTS

| | | |
|---|---|---|
| 0 105 812 | 4/1984 | European Pat. Off. ........ A61B 10/00 |
| 0 483 005 | 4/1992 | European Pat. Off. . |
| 0 581 704 | 2/1994 | European Pat. Off. . |
| 2335576 | 1/1975 | Germany . |
| 32 26 976 | 2/1983 | Germany . |
| 32 22 053 | 12/1983 | Germany ....................... A61B 10/00 |
| 32 27 624 | 1/1984 | Germany ....................... A61B 10/00 |
| 34 05 537 | 8/1985 | Germany ........................ A61B 8/00 |
| 3447444 | 7/1986 | Germany . |
| 40 37 387 | 5/1992 | Germany ........................ A61B 8/00 |
| 896 539 | 4/1980 | U.S.S.R. . |
| 2 094 590 | 9/1982 | United Kingdom . |
| WO 83/02053 | 6/1983 | WIPO ............................. A61B 10/00 |
| 88/08272 | 11/1988 | WIPO . |
| 89/11248 | 11/1989 | WIPO . |
| 94/21189 | 9/1994 | WIPO . |
| 95/11627 | 5/1995 | WIPO . |

OTHER PUBLICATIONS

Magnusson, A., "New Stereotactic Instrument Facilitates Computer Tomographically Guided Punctio", Läkartidningen, vol. 86, No. 21, pp. 1885–1886, 1888 (1988).

Gardineer et al., "Video–photographic System for Rapid Inexpensive Unit Recording and Flexible Replay of Real–time Ultrasonic Imaging of the Breast", SPIE vol. 273, Appln. of Optical Instrumentation in Medicine IX, pp. 343–347 (1981).

Darla Haight et al., "Radiologists Spread Their Wings: A Look at the Possibilities in STereotactic Breast Biopsy", Admin. Rad. J., pp. 87–89 (Nov. 1987).

E. Azavedo et al., "Stereotactic Fine–Needle Biopsy in 2594 Mammographically Detected Non–Palable Lesions", The Lancet, pp. 1033–1036 (May 1989).

Gunilla Svane, MD., "Stereotactic Needle Biopsy", Dept. of Dianostic Radioloyg at the Karolinska Hospital, Stockholm, Sweden (1987).

Gillian Newstead, MD., "When and When Not to Biopsy the Breast", Diagnostic Imaging, pp. 111–116, (Mar. 1993).

(List continued on next page.)

*Primary Examiner*—William E. Kamm
*Assistant Examiner*—George R. Evanisko

[57] ABSTRACT

Apparatus and methods are provided for positioning a needle or cannula of a biopsy device for insertion into a tissue mass by correlating, in real-time, the actual needle or cannula position prior to insertion with its probable trajectory once inserted. In a preferred embodiment, a biopsy device support block is mechanically coupled to an ultrasound transducer to provide alignment of the biopsy device with the ultrasound image in at least one plane. Continued ultrasound scanning of a selected trajectory may be provided to assess depth of penetration of the needle or cannula of the biopsy device, when inserted.

16 Claims, 5 Drawing Sheets

U.S. PATENT DOCUMENTS

| | | |
|---|---|---|
| 3,480,002 | 11/1969 | Flaherty et al. . |
| 3,556,081 | 1/1971 | Jones . |
| 3,589,361 | 6/1971 | Loper . |
| 3,609,355 | 9/1971 | Kwarzen . |
| 3,765,403 | 10/1973 | Brenden .................................. 128/2 V |
| 3,921,442 | 11/1975 | Soloway . |
| 3,939,696 | 2/1976 | Kossoff . |
| 3,963,933 | 6/1976 | Henkes, Jr. .............................. 250/456 |
| 3,971,950 | 7/1976 | Evans et al. ............................. 250/451 |
| 3,973,126 | 8/1976 | Redington et al. . |
| 3,990,300 | 11/1976 | Kossoff . |
| 3,991,316 | 11/1976 | Schmidt et al. . |
| 4,021,771 | 5/1977 | Collins et al. . |
| 4,051,380 | 9/1977 | Lasky . |
| 4,058,114 | 11/1977 | Soldner .................................. 128/2 V |
| 4,094,306 | 6/1978 | Kossoff . |
| 4,099,880 | 7/1978 | Kano . |
| 4,167,180 | 9/1979 | Kossoff . |
| 4,206,763 | 6/1980 | Pedersen . |
| 4,249,541 | 2/1981 | Pratt . |
| 4,285,010 | 8/1981 | Wilcox . |
| 4,347,850 | 9/1982 | Kelly-Fry et al. . |
| 4,363,326 | 12/1982 | Kopel ................................ 128/662.05 |
| 4,369,284 | 1/1983 | Chen . |
| 4,402,324 | 9/1983 | Lindgren et al. . |
| 4,433,690 | 2/1984 | Green et al. ............................ 128/660 |
| 4,434,799 | 3/1984 | Taenzer . |
| 4,455,872 | 6/1984 | Kossoff et al. . |
| 4,465,069 | 8/1984 | Barbier et al. . |
| 4,469,106 | 9/1984 | Harui . |
| 4,485,819 | 12/1984 | Igl .......................................... 128/660 |
| 4,497,325 | 2/1985 | Wedel . |
| 4,501,278 | 2/1985 | Yamaguchi et al. . |
| 4,527,569 | 7/1985 | Kolb . |
| 4,541,436 | 9/1985 | Hassler et al. . |
| 4,545,385 | 10/1985 | Pirschel . |
| 4,573,180 | 2/1986 | Summ . |
| 4,579,123 | 4/1986 | Chen et al. . |
| 4,583,538 | 4/1986 | Onik et al. . |
| 4,592,352 | 6/1986 | Patil . |
| 4,599,738 | 7/1986 | Panetta et al. ............................ 378/37 |
| 4,608,989 | 9/1986 | Drue . |
| 4,613,122 | 9/1986 | Manabe . |
| 4,613,982 | 9/1986 | Dornheim et al. . |
| 4,618,213 | 10/1986 | Chen . |
| 4,618,973 | 10/1986 | Lasky . |
| 4,625,555 | 12/1986 | Fujii .......................................... 73/597 |
| 4,671,292 | 6/1987 | Matzuk . |
| 4,681,103 | 7/1987 | Boner et al. . |
| 4,686,997 | 8/1987 | Oloff et al. . |
| 4,722,346 | 2/1988 | Chen . |
| 4,727,565 | 2/1988 | Ericson . |
| 4,733,661 | 3/1988 | Palestrant . |
| 4,735,215 | 4/1988 | Goto et al. . |
| 4,750,487 | 6/1988 | Zanetti . |
| 4,774,961 | 10/1988 | Carr . |
| 4,784,134 | 11/1988 | Arana . |
| 4,791,934 | 12/1988 | Brunnett . |
| 4,821,727 | 4/1989 | Levene et al. .......................... 128/653 |
| 4,844,080 | 7/1989 | Frass et al. . |
| 4,862,893 | 9/1989 | Martinelli .......................... 128/662.03 |
| 4,869,247 | 9/1989 | Howard, III et al. . |
| 4,875,478 | 10/1989 | Chen .................................. 128/303 B |
| 4,890,311 | 12/1989 | Saffer . |
| 4,898,178 | 2/1990 | Wedel . |
| 4,899,756 | 2/1990 | Sonek ................................ 128/662.05 |
| 4,911,173 | 3/1990 | Terwilliger . |
| 4,930,143 | 5/1990 | Lundgren et al. . |
| 4,940,061 | 7/1990 | Terwilliger et al. . |
| 4,944,308 | 7/1990 | Akerfeldt . |
| 4,953,558 | 9/1990 | Akerfeldt . |
| 4,962,515 | 10/1990 | Kopans . |
| 4,962,752 | 10/1990 | Reichenberger et al. . |
| 4,966,152 | 10/1990 | Gang et al. ......................... 128/661.07 |
| 4,981,142 | 1/1991 | Dachman . |
| 5,003,979 | 4/1991 | Merickel et al. . |
| 5,007,428 | 4/1991 | Watmough ......................... 128/660.04 |
| 5,029,193 | 7/1991 | Saffer . |
| 5,056,523 | 10/1991 | Hotchkiss, Jr. et al. ................ 606/130 |
| 5,078,142 | 1/1992 | Siczek ................................. 128/653.1 |
| 5,078,149 | 1/1992 | Katsumata et al. . |
| 5,083,305 | 1/1992 | Tirelli et al. . |
| 5,095,910 | 3/1992 | Powers . |
| 5,099,503 | 3/1992 | Strömmer . |
| 5,107,843 | 4/1992 | Aarnio et al. . |
| 5,113,420 | 5/1992 | Davis, Jr. et al. ......................... 378/20 |
| 5,158,088 | 10/1992 | Nelson et al. ..................... 128/662.05 |
| 5,199,056 | 3/1993 | Darrah . |
| 5,205,297 | 4/1993 | Montecalvo et al. . |
| 5,219,351 | 6/1993 | Teubner et al. . |
| 5,260,871 | 11/1993 | Goldberg . |
| 5,262,468 | 11/1993 | Chen . |
| 5,273,435 | 12/1993 | Jacobson . |
| 5,280,427 | 1/1994 | Magnusson et al. . |
| 5,305,365 | 4/1994 | Coe . |
| 5,318,028 | 6/1994 | Mitchell et al. . |
| 5,361,768 | 11/1994 | Webler et al. . |
| 5,379,769 | 1/1995 | Ito et al. . |
| 5,386,447 | 1/1995 | Siczek . |
| 5,396,897 | 3/1995 | Jain et al. . |
| 5,411,026 | 5/1995 | Carol . |
| 5,415,169 | 5/1995 | Siczek et al. . |
| 5,426,685 | 6/1995 | Pellegrino et al. . |
| 5,433,202 | 7/1995 | Mitchell et al. . |
| 5,447,154 | 9/1995 | Cinquin et al. . |
| 5,450,851 | 9/1995 | Hancock . |
| 5,474,072 | 12/1995 | Shmulewitz . |
| 5,479,927 | 1/1996 | Shmulewitz . |
| 5,487,387 | 1/1996 | Trahey et al. . |
| 5,488,952 | 2/1996 | Schoolman . |
| 5,499,989 | 3/1996 | LaBash . |
| 5,506,877 | 4/1996 | Niklason et al. . |
| 5,522,787 | 6/1996 | Evans . |
| 5,524,636 | 6/1996 | Sarvazyan et al. . |
| 5,594,769 | 1/1997 | Pellegrino et al. . |
| 5,595,177 | 1/1997 | Mena et al. . |
| 5,603,326 | 2/1997 | Richter . |
| 5,609,152 | 3/1997 | Pellegrino et al. . |
| 5,640,956 | 6/1997 | Getzinger et al. . |
| 5,660,185 | 8/1997 | Shmulewitz et al. . |
| 5,664,573 | 9/1997 | Shmulewitz et al. . |

OTHER PUBLICATIONS

Jan Bolmgren, et al., "Stereotaxic Instrument for Needle Biopsy of the Mamma", (Sweden) J. Radiology, 129:121–125 (Jul. 1977).

Kambiz Dowlatshahi, MD, Breast Care: "The Needle Replaces The Knife" (Exploring Sterotactic Guided Needle Biopsy), Admin. Radiology, pp. 28–31 (Jun. 1989).

Ralph Mösges et al., "Multimodal Information for Computer–Integrated Surgery", Mösges & Lavallée: Multimodal Information for CIS/Data Acquisition & Segmentation, pp. 5–19.

P.N.T. Wells et al., "Tumor detection by ultrasonic Doppler blood–flow signals", Ultrasonics, pp. 231–232 (Sep. 1977).

W. Phil Evans, MD et al., "Needle Localization and Fine––Needle Aspiration Biopsy of Nonpalpable Breast Lesions with use of Standard and Stereotactic Equipment", Radiology, 173:53–56 (1989).

S.H. Parker et al., "Percutaneous Large–Core Breast Biopsy: A Multi–institutional Study," *Radiology*, Nov. 1994, pp. 359–364.

S.H. Parker et al., "US–guided Automated Large–Core Breast Biopsy", *Radiology*, May 1993, 507–511.

E. Rubin, "Breast Cancer in the 90's", *Applied Radiology*, Mar. 1993, pp. 23–26.

G. Newstead, "When and when not to biopsy the breast", *Diagnostic Imaging*, Mar. 1993, pp. 111–116.

R.F. Brem and O.M.B. Gatewood, "Template–guided Breast US", *Radiology*, Sep. 1992, pp. 872–874.

B.D. Fornage et al., "Ultrasound–Guided Needle Biopsy Of THe Breast And Other Interventional Procedures," *Radiologic Clinics Of North America*, vol. 30, No. 1, Jan. 1992, pp. 167–185.

W.F. Conway et al., "Occult Breast Masses: Use of a Mammographic Localizing Grid for US Evaluation", *Radiology*, Oct. 1991, pp. 143–146.

E.B. Mendelson, "Ultrasound secures place in breast Ca management", *Diagnostic Imaging*, Apr. 1991, pp. 120–129.

V.P. Jackson, "The Role of US in Breast Imaging", *Radiology*, Nov. 1990, pp. 303–311.

S.H. Parker and W.E. Jobe, "Large–core Breast Biopsy Offers Reliable Diagnosis," reprinted from *Diagnostic Imaging*, Oct. 1990.

F.M. Hall, "Mammographic Second Opinions Prior to Biopsy of Nonpalpable Breast Lesions", *Arch. Surg.*, Mar. 1990, pp. 298–299.

K. Dowlatshahi et al., "Nonpalpable Breast Tumors: Diagnostic with Stereotaxic Localization and Fine Needle Aspiration", *Radiology*, Feb. 1989, pp. 427–433.

B.D. Fornage et al., "Breast Masses: US–Guided Fine Needle Aspiration Biopsy", *Radiology*, Feb. 1987, pp. 409–414.

I. Andersson, "Mammography in Clinical Practice", *Medical Radiography and Photography*, vol. 62, No. 2, (1986) (Eastman Kodak Co.).

IMAGE-GUIDED BIOPSY APPARATUS AND METHODS OF USE

REFERENCE TO RELATED APPLICATIONS

This application is a continuation-in-part of U.S. patent application Ser. No. 08/421,381, filed Apr. 13, 1995, U.S. Pat. No. 5,660,185 entitled "IMAGE-GUIDED BIOPSY APPARATUS WITH ENHANCED IMAGING AND METHODS."

BACKGROUND OF THE INVENTION

This invention relates to methods and apparatus for conducting an examination of breast tissue and for performing image-guided biopsy of that tissue.

Previously known biopsy methods range from minimally invasive techniques, such as fine needle aspiration (using, for example, a 21 gauge hypodermic needle) and large core biopsy (using, for example, a 14 gauge needle mounted in an automated biopsy gun), to open-procedures in which the lesion is surgically excised. Minimally invasive techniques are faster, less expensive, safer and less traumatic for the patient than surgical excision, and have begun developing widespread acceptance.

A concern common to previously known minimally invasive biopsy techniques, however, is ensuring that the biopsy needle actually obtains a tissue sample from the suspected lesion, rather than adjacent healthy tissue. Previously known techniques that attempt to ensure that the biopsy needle trajectory enters the region of the suspected lesion are described, for example, in Fornage et al., "Ultrasound-Guided Needle Biopsy Of The Breast And Other Interventional Procedures," Radiologic Clinics Of North America, Vol. 30, No. 1 (January 1992), Fornage et al. "Breast Masses: US-Guided Fine Needle Aspiration Biopsy," Radiology, 162:409–414 (February 1987), Parker et al., "US-guided Automated Large-Core Breast Biopsy," Radiology, 187:507–511 (May 1993), and Parker and Jobe, "Large-Core Breast Biopsy Offers Reliable Diagnosis," *Diagnostic Imaging* (October 1990).

The foregoing articles describe a free-hand ultrasound technique, in which insertion of a biopsy needle into a suspected lesion is performed by holding a linear array ultrasound transducer in one hand and inserting the needle into the tissue with the other hand. In particular, the ultrasound transducer is held above the midline of the suspicious mass and the needle (or needle of the automated biopsy gun) is then inserted in the tissue near the base of the transducer, so that the tip of the needle appears in the ultrasound scan. In addition, when a biopsy gun is employed, additional personnel may be required to steady the biopsy gun during use or to hold the ultrasound transducer.

As described in the Fornage et al. articles and Parker et al. article, difficulties arise using the free-hand technique where the suspected lesion is located near the patient's chest wall, or in proximity to a prothesis. These articles also emphasize that the practitioner's level of skill in using the free-hand technique can dramatically influence the results obtained. All of the foregoing articles reject the use of biopsy needle guides that can be attached to the ultrasound transducer, because the guides are said to interfere with the flexibility and maneuverability required to obtain satisfactory results.

The Parker and Jobe article also describes stereotactic mammographic biopsy systems. In such systems, two X-ray images of the breast tissue are made at different angles, thereby permitting the coordinates of a lesion to be calculated. The biopsy needle, typically an automated biopsy gun (e.g., Biopty from C. R. Bard, Inc., Bard Urological Division, Covington, Ga.) mounted in a rigid housing attached to the biopsy table, is moved to the calculated coordinates and actuated. Two additional X-ray views of the breast tissue are then taken to confirm that the needle has actually sampled the region of the suspected lesion. That article further describes that in stereotactic systems breast movement may render earlier stereo calculations of little use.

A drawback common to all of the stereotactic systems, however, is the need for multiple X-rays of the tissue, thus exposing the tissue to potentially unhealthful ionizing radiation. These systems also provide no real-time imaging of the needle trajectory, so as described in the Parker and Jobe article, intervening movement of the breast tissue may render the calculated coordinates useless and result in a potentially misleading biopsy sample. Indeed, the clinician is not even aware that the biopsy needle missed the intended target until after the follow-up stereotactic views are taken.

Moreover, because the biopsy needle is secured in a fixed housing so as to provide a fixed trajectory for biopsy needle, stereotactic systems provide no freedom of movement for the biopsy needle relative to the target tissue. Consequently, several needle insertions and withdrawals are required to adequately characterize the tissue.

A major disadvantage of the above-described previously known methods and apparatus arises due to the inability of the clinician to estimate, in real-time, the correct trajectory of the biopsy needle from the breast surface to the region of the suspected tumor or lesion. Even when guided by free-hand ultrasound scanning, the clinician typically must insert and withdraw the biopsy needle numerous times to improve the confidence level that a portion of the suspected lesion has been collected. Then, each of the needle aspiration samples must be separately tested, significantly increasing the overall cost of the procedure.

Likewise, in stereotactic systems, the inability to monitor tissue movement and to manipulate the biopsy needle once inserted, creates the need for multiple needle insertions to obtain adequate characterization of the suspected lesion. And again, each of these multiple samples must be individually tested to properly characterize the suspected lesion.

Such repetitive insertion and withdrawal of the biopsy needle may cause significant patient discomfort. Moreover, in those cases where the biopsy indicates no need for treatment by surgical methods, the repeated biopsy needle insertion may nevertheless leave the patient with cosmetically unappealing scar tissue.

In view of the foregoing, it would be desirable to provide apparatus and methods by which a biopsy needle could be positioned for insertion so as to have a real-time, predetermined trajectory to a targeted tissue region, thereby reducing the need for repetitive needle insertion and withdrawal to obtain a satisfactory biopsy sample.

It would also be desirable to provide apparatus and methods by which a biopsy needle could be positioned for insertion into tissue along a predetermined trajectory, as in stereotactic apparatus, but which enables the clinician to alter that trajectory once the needle has been inserted, so as to reduce the number of scars resulting from repetitive skin punctures.

SUMMARY OF THE INVENTION

In view of the foregoing, it is an object of this invention to provide apparatus and methods by which a biopsy needle can be positioned for insertion so as to have a predetermined trajectory to a targeted tissue region which can be observed and verified in real time, thereby reducing the need for repetitive needle insertion and withdrawal to obtain a satisfactory biopsy sample.

It is a further object of the present invention to provide apparatus and methods by which a biopsy needle can be positioned for insertion into tissue along a predetermined trajectory, and which enables the clinician to alter that trajectory once the needle has been inserted, so as to reduce the number of scars resulting from repetitive skin punctures.

It is yet another object of this invention to provide more economical solutions for image guided biopsy, which employ conventional ultrasound transducers and rely on mechanical coupling of the ultrasound transducer and the biopsy needle to maintain alignment of the ultrasound transducer and biopsy needle in at least one plane.

These and other objects of the invention are accomplished in accordance with the principles of the invention by providing a biopsy system that permits an ultrasound transducer to be mechanically coupled to a biopsy needle so that the biopsy needle is retained in alignment with the plane of the ultrasound image generated by the ultrasound transducer.

Apparatus constructed in accordance with the present invention includes at least a first compression surface, an ultrasound transducer holder and a biopsy needle support, the ultrasound transducer holder and the biopsy needle support mechanically aligned in at least one plane.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
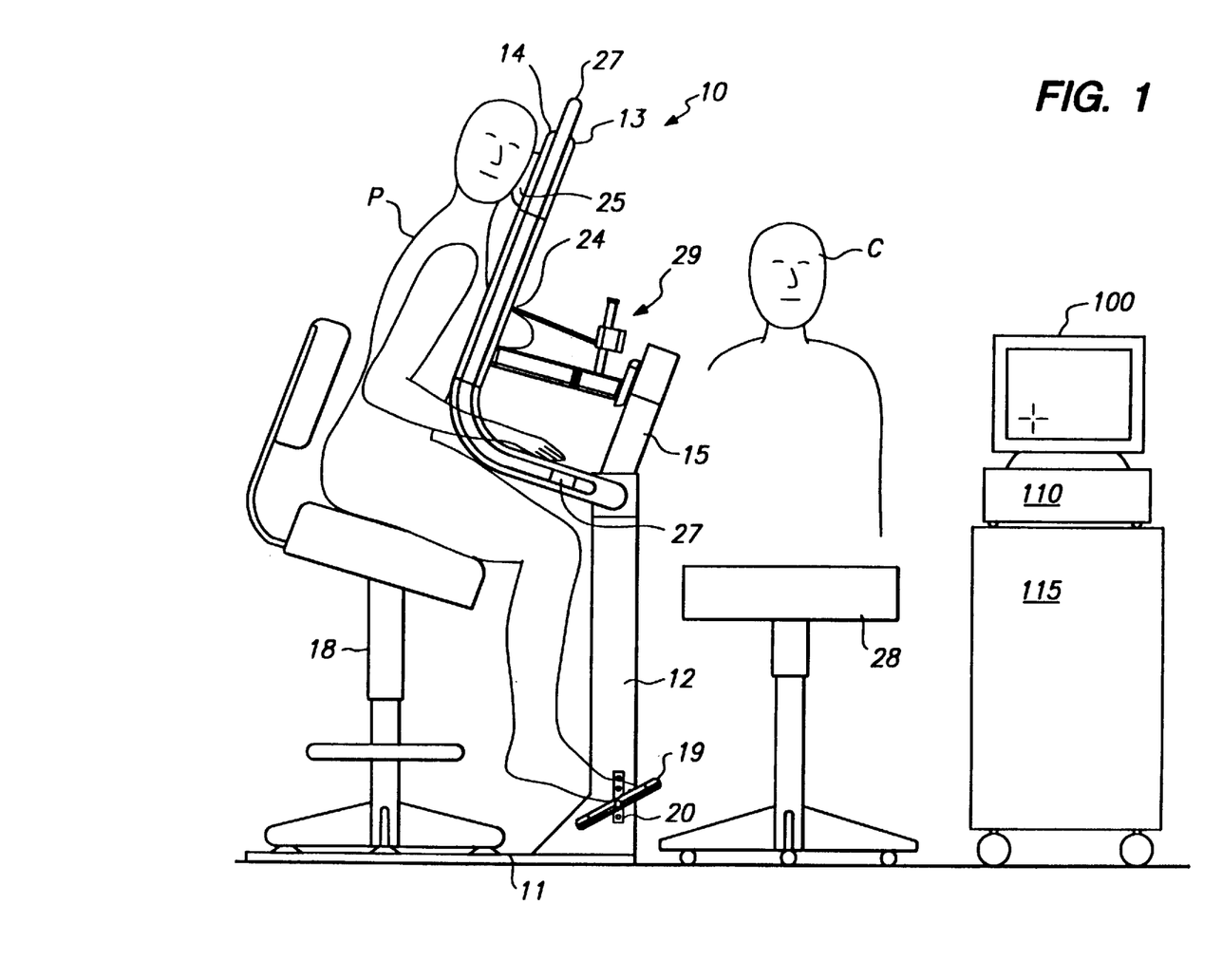
FIG. 1 is an elevation view of an illustrative embodiment of a patient support stand suitable for use with the biopsy system of the present invention.

Referring to FIG. 1, an illustrative embodiment of a patient support apparatus or stand 10 suitable for use with the biopsy system of the present invention is described. Stand 10 comprises base 11, vertical pillar 12, frame 13 supporting patient bearing surface 14 and biopsy support column 15.

Stand 10 includes opening 24 in the patient bearing surface 14 so that a breast of the patient may extend therethrough, while the patient's torso is supported by frame 13 and patient bearing surface 14. Vertical pillar 12 carries foot supports 19 which may be vertically adjustably positioned in holes 20 on vertical pillar 12 to accommodate the patient's height. Head rest 25 is provided on patient bearing surface 14 to support the patient's head, and hand rail 27 is provided around the periphery of frame 13 to assist the patient is orienting herself with respect to stand 10. Further details of stand 10 are provided in concurrently filed, commonly assigned, copending U.S. patent application Ser. No. 08/680,559.

Image-guided biopsy system 29, described hereinafter, is rotatably connected to biopsy support column 15 for rotation about an axis located parallel to the plane of the compression surfaces of the imaging system, thus enabling image-guided biopsy system 29 to be rotated with respect to the tissue extended through opening 24 of patient bearing surface.

Patient P is seated on chair 18 so that a breast extends through an opening 24 in the patient support surface for examination and biopsy by clinician C seated on chair 28 behind stand 10. Images generated by image-guided biopsy system 29 are displayed on display 100 of image processing system 110 located on cart 115. In an alternative embodiment, the electronics and image processing system 110 may be incorporated into stand 10, for example, in vertical pillar 12, while display 100 may be mounted on a suitable support attached to stand 10, thereby eliminating use of separate cart 115. In either embodiment, patient P may be aware of the presence of the clinician C behind stand 10 when the patient is seated on chair 18, but the patient cannot directly view the activities of the clinician, since her view of the breast extended through opening 24 is shielded by patient bearing surface 14 and frame 13.

Figure 2A:
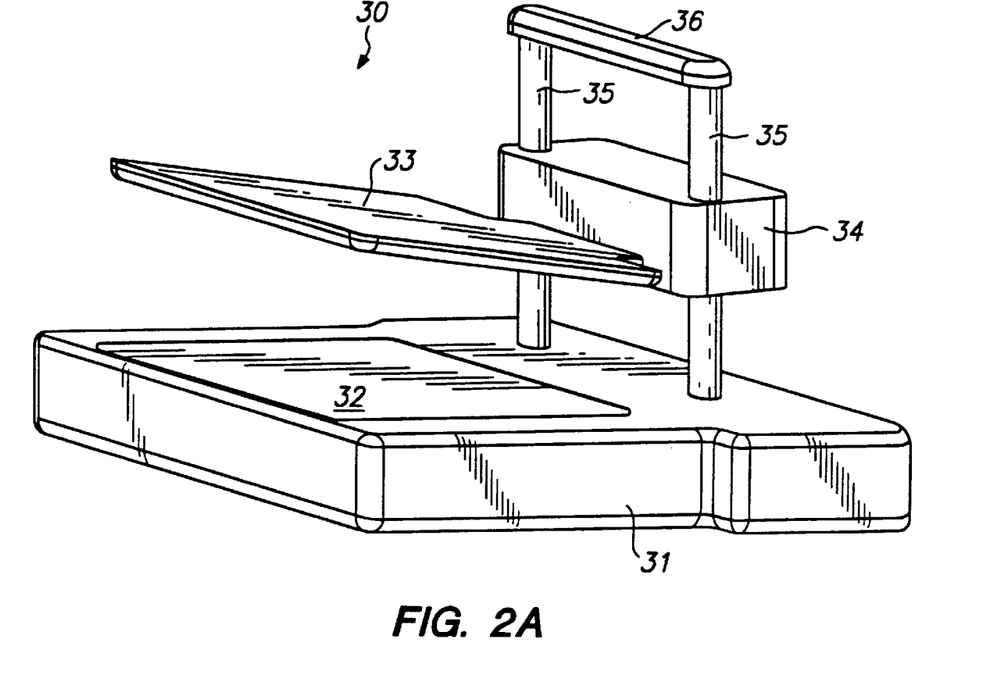
FIGS. 2A and 2B are, respectively, perspective and side views of a the tissue compression arrangement suitable for use with imaging and biopsy apparatus of the present invention.
Figure 2B:
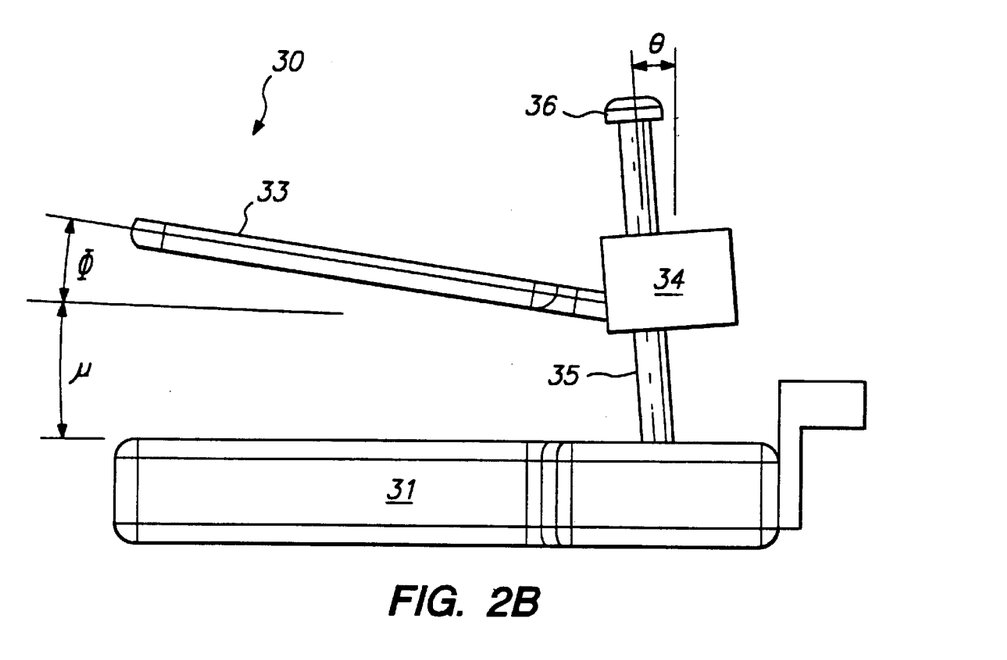

Referring now to FIGS. 2A and 2B, an illustrative arrangement for compressing the breast extended through opening 24 of stand 10 is described. Applicant has determined that the arrangement of compression surfaces illustrated in FIGS. 2, can beneficially induce traction in the patient's breast and adjoining tissue that draws the tissue away from the patient's chest during compression.

Compression arrangement 30 comprises housing 31 including sonolucent lower compression plate 32 and upper compression plate 33 affixed to slide block 34. Slide block 34 is adjustably supported on bars 35, for example, by threaded bars or a lockable rack and pinion type drive, so that top block 36 limits the travel of slide block 34 away from enclosure 31. Slide block 34 may be moved on bars 35 using either a manual or motor-driven arrangement. Housing 31 encloses an ultrasound transducer, supported as described hereinafter, that is acoustically coupled to the underside of lower compression plate 32 to provide ultrasonic images of tissue captured between lower compression plate 32 and upper compression plate 33.

Lower compression plate 32 is preferably formed of a sonolucent material, such as Surlyn® ionomers, such as Surlyn® 8940, available from E. I. Du Pont de Nemours and Company, Wilmington, Del., or a polymethyl pentene, such as TPX® MX-002 and MX-004, available from Mitsui & Co., Tokyo, Japan, while upper compression plate 33 may be formed of a sonolucent material, or may be of conventional construction. A gel pad (not shown), may be used to enhance acoustic coupling between lower compression plate 32 and the tissue, as described in commonly assigned U.S. Pat. No. 5,479,927.

Figure 3A:
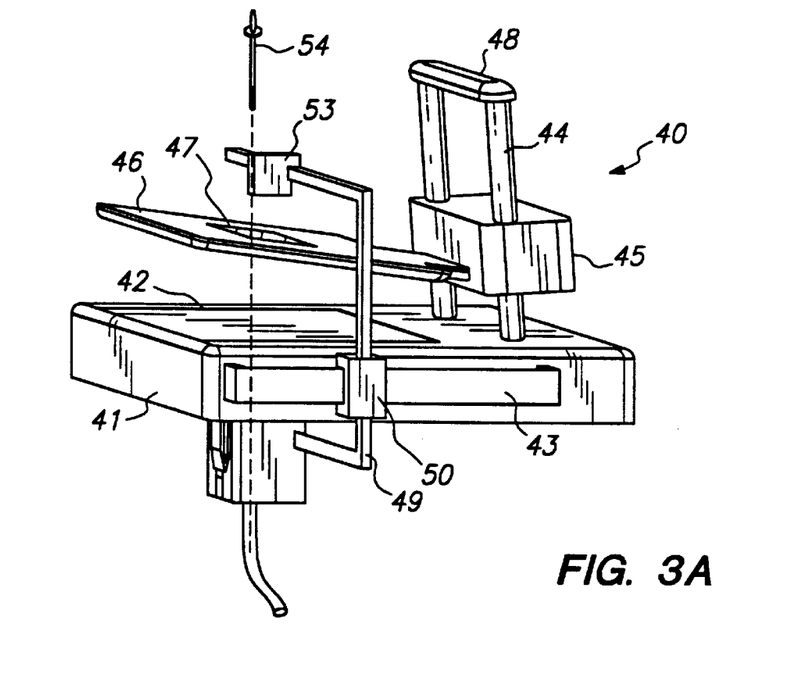
FIGS. 3A and 3B are, respectively, perspective and front sectional views of a first illustrative imaging and biopsy apparatus constructed in accordance with the present invention.

As depicted in FIG. 2A, upper compression plate 33 may be of approximately the same size as lower compression plate 32, thereby compressing the entirety of the patient's breast to a substantially uniform or, as described below, gradually tapered, thickness. Alternatively, upper compression plate may be constructed as shown in FIG. 3A to form a frame surrounding a central aperture. In yet further alternative embodiments, upper compression plate 33 may have a substantially smaller area than lower compression plate 32, thereby providing compression over only a localized region of the patient's breast. Such a "spot" compression plate might have an area similar to that of the aperture depicted in FIG. 3A, so that the area of the upper compression plate is only one-half to one-quarter of the area of lower compression plate 32.

Referring again to FIG. 2B, support bars 35 on which slide block 34 is disposed are canted forward by an angle $\Theta$ of up to about 15 degrees, and preferably about 4 degrees from a plane parallel to the patient's chest wall. Upper compression plate 33 is inclined at an angle $\Phi$ of up to about 45 degrees, and preferably 4 degrees, from a plane orthogonal to the patient's chest wall. Lower compression surface 32 is angled downward, at its proximal edge, at an angle $\mu$ of up to 90 degrees, and preferably 4 degrees, from a plane orthogonal to the patient's chest wall. In one intended use of the ultrasonic scanner of the present invention, wherein the angle $\mu$ is 90 degrees, upper compression plate 33 and bars 35 are removed so that lower compression surface 32 may be pressed directly against the patient's chest wall, for example, for imaging features within the chest wall.

Applicant has determined that by canting support bars 35 towards the patient by an angle $\Theta$, and by inclining the upper compression plate by an angle $\Phi$, a state of traction can be induced in the patient's tissue that draws the tissue away from the patient's chest wall, thereby enhancing the capability to image tissue near the patient's chest wall.

The traction effect induced by the above described system is accomplished as follows: First, the patient inserts the tissue to be examined between the upper compression plate 33 and lower compression plate 32. Next, upper compression plate 32 is lowered by moving slide block 34 down support bars 35 until upper compression plate 33 contacts the tissue. As slide block 34 and upper compression plate 33 are urged further towards lower compression plate 32, the tissue becomes flattened. Due to the cant of support bars 35, continued downward movement of upper compression plate 33 causes the upper compression plate to be displaced away from the patient's chest wall, thereby inducing a traction force in the tissue contacting the upper compression plate. This traction force tends to pull the tissue away from the chest wall, permitting enhanced imaging capability.

In addition, applicants have determined that the above-described traction effect can be further enhanced by providing the lower surface of upper compression plate 33 with a slightly roughened or tacky surface, so that the breast adheres to the surface. The gel pad described above for coupling the breast tissue to the ultrasonic scanner provides a similar functionality for lower compression plate 32.

Applicants' invention represents a subtle but significant departure from previously known compression arrangements, wherein the compression plates typically move orthogonally during the tissue compression step. In such previously known systems, when a compressive load is imposed on the tissue, the tissue is generally forced outwardly. This in turn causes the tissue near the chest wall to be forced inwardly, i.e., inward through the patient's chest wall. As described hereinabove, the method of canting and inclining the components of the imaging system provides improved imaging capability with respect to previously known systems.

In particular, the method of the present invention of angling the lower compression plate slightly towards the patient's chest wall (with respect to a plane orthogonal to the chest wall), enables the ultrasound scanner to image tissue close to, or within, the patient's chest wall, depending upon the angle $\mu$ selected.

Figure 3B:
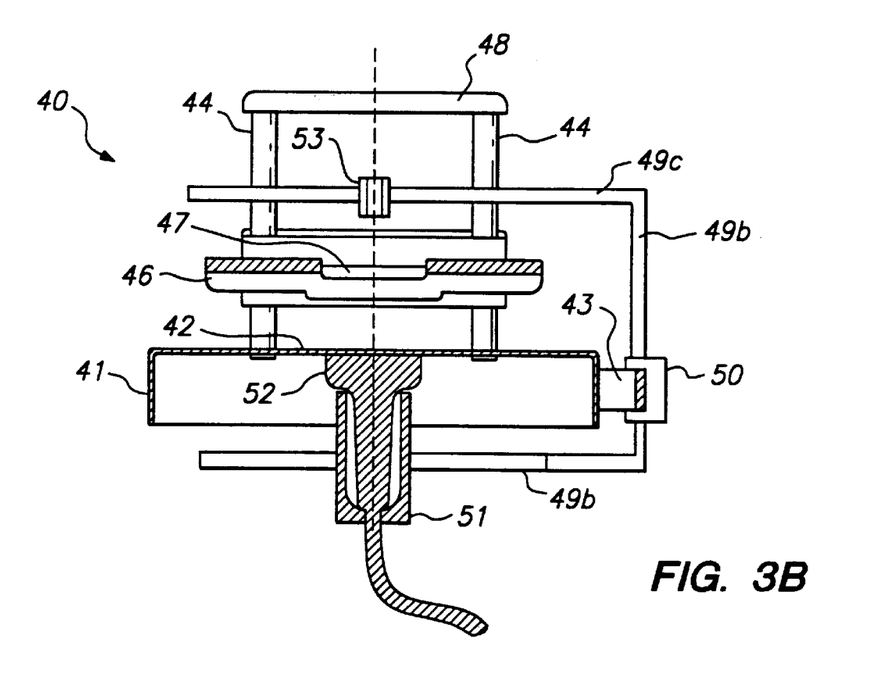
Figure 4A:
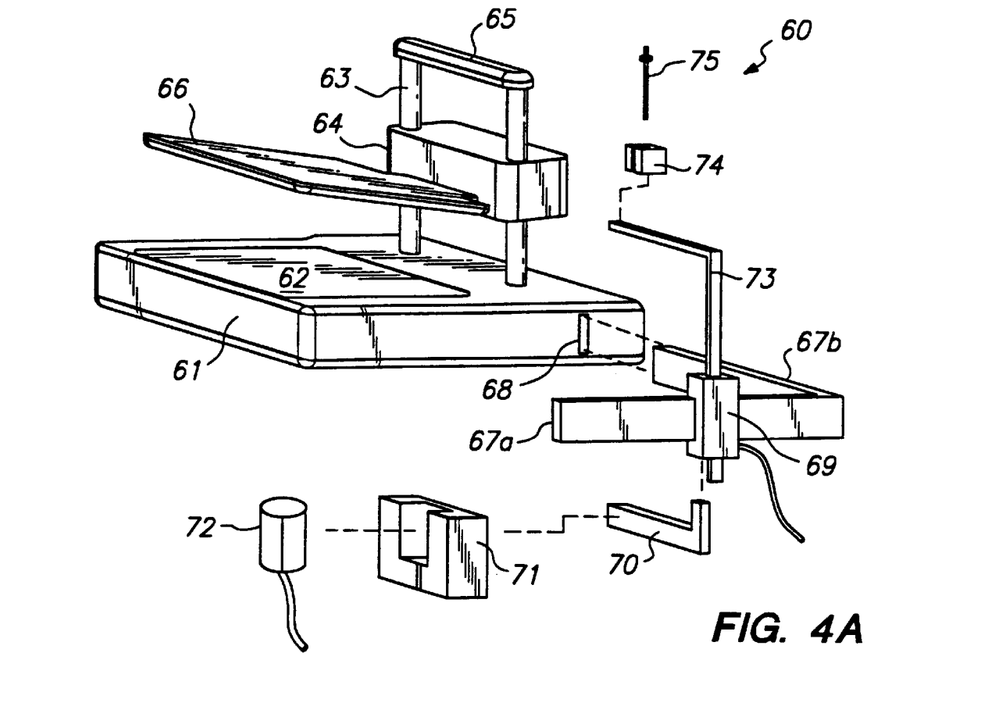
FIGS. 4A and 4B are, respectively, perspective and front sectional views of a second illustrative imaging and biopsy apparatus constructed in accordance with the present invention.
Figure 4B:
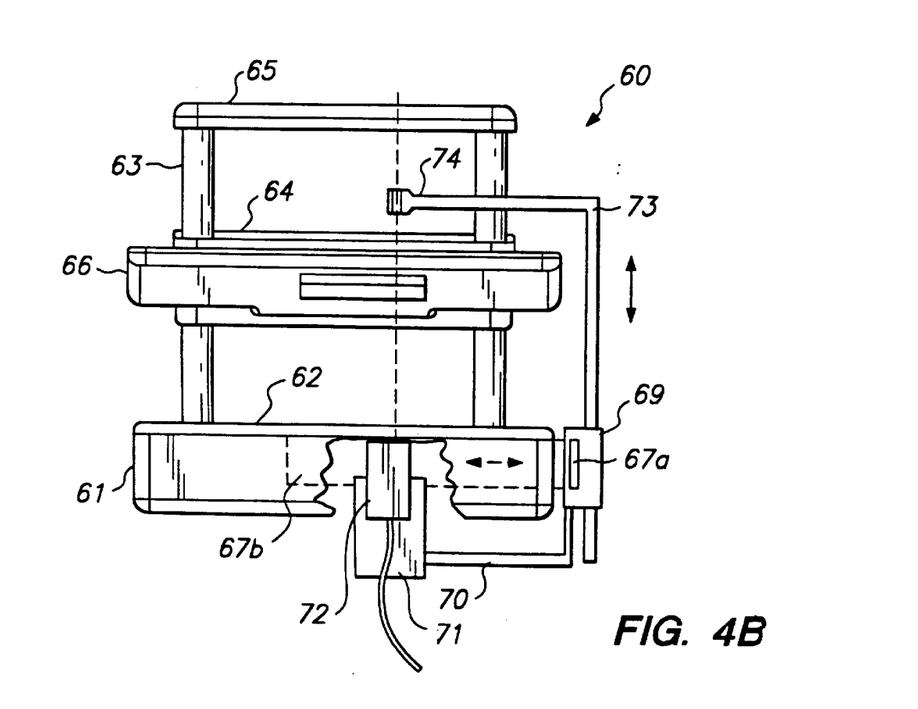
Figure 5A:
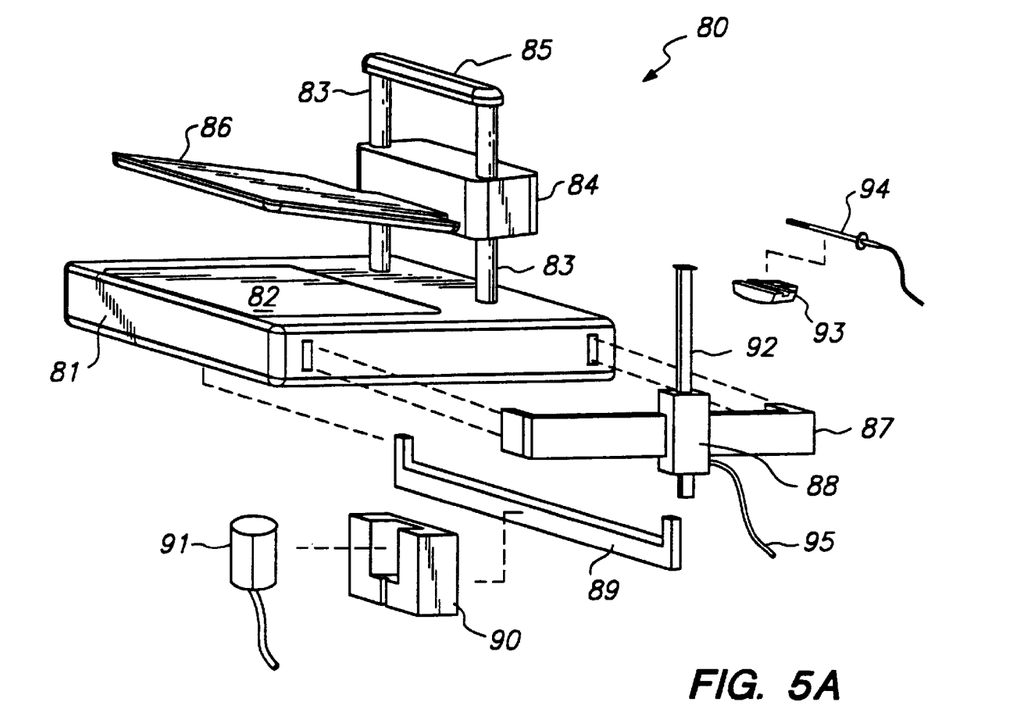
FIGS. 5A and 5B are, respectively, perspective and front sectional views of a third illustrative imaging and biopsy apparatus constructed in accordance with the resent invention.
Figure 5B:
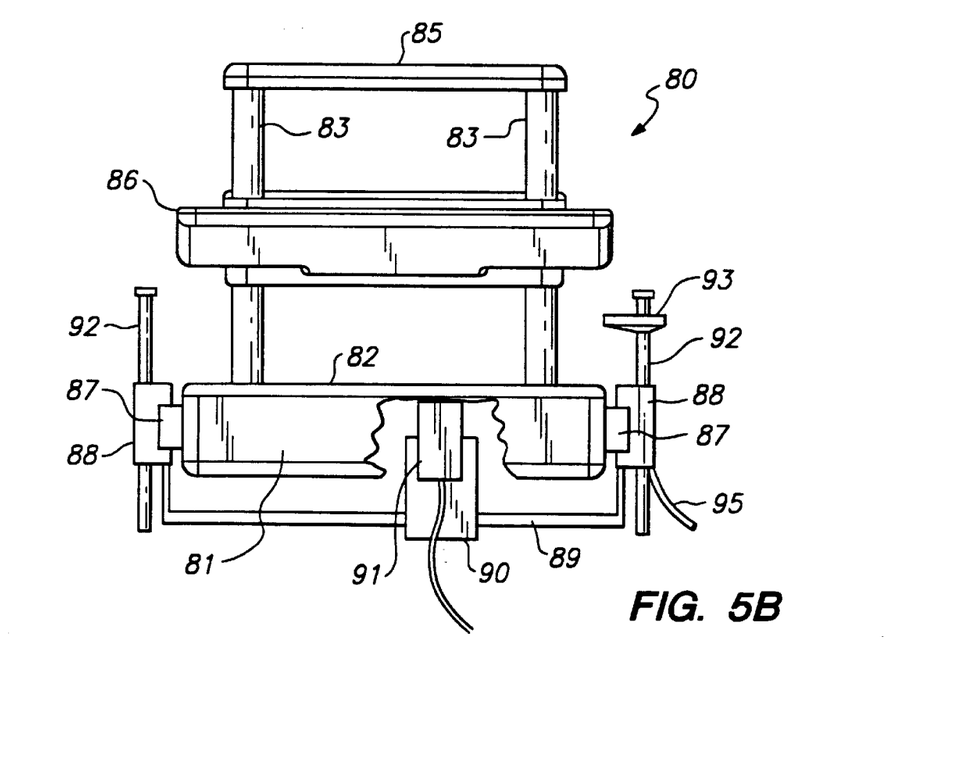

Referring now to FIGS. 3 through 5, illustrative biopsy systems constructed in accordance with the principles of the present invention are described. These biopsy systems provide the capability to perform a biopsy under the guidance of real-time ultrasonic images of the tissue, which may be monitored by clinician C on display 100.

In accordance with the principles of the present invention, the needle or cannula of a biopsy device is guided to a target location within the patient's tissue using ultrasonic images displayed on display 100 monitored by the clinician. Thus, the needle or cannula trajectory may be determined prior to actual insertion of the device into the tissue, thereby reducing the need for repeatedly inserting and withdrawing the device to obtain samples of a suspected lesion.

With respect to FIGS. 3A and 3B, a first embodiment of image-guided biopsy system 40 constructed in accordance with the present invention is described. Biopsy system 40 includes rigid housing 41 including sonolucent lower compression plate 42 and guide arm 43. Support bars 44 are affixed to housing 41 and vertically adjustably support slide block 45 and upper compression plate 46. Upper compression plate 46 includes window 47 through which the needle or cannula of a biopsy device may be inserted, as described hereinafter. Top block 48 limits upward travel of slide block 45 on support bars 44. Support bars 44 are canted forward by an angle $\Theta$, upper compression plate is inclined at an angle $\Phi$, and lower compression plate 42 is angled downward by at an angle $\mu$, as described hereinabove with respect to FIGS. 2.

Guide arm 43 includes a C-shaped support arm 49 which is fastened to slide block 50. Slide block 50 is disposed for proximal and distal movement along guide arm 43. C-shaped support arm 49 includes lower arm 49a, vertical arm 49b and upper arm 49c. Lower arm 49a carries holder 51 which is configured to hold an ultrasound transducer 52 so that it is acoustically coupled to the underside of lower compression plate 42.

Upper arm 49c includes biopsy device support block 53, for removably carrying a biopsy device, illustratively, biopsy needle 54. Exemplary biopsy device support blocks are described in copending commonly assigned U.S. patent application Ser. No. 08/421,381, which is incorporated herein by reference. Biopsy device support block 53 on C-shaped support arm 49 holds the needle or cannula of a biopsy device so that it is aligned with ultrasound transducer 52. As will of course be understood by those of skill in the art, biopsy device could alternatively be a biopsy gun, such as the aforementioned BIOPTY offered by C. R. Bard, Inc., Covington, Ga., or the ABBI biopsy device offered by U.S. Surgical Corporation, Norwalk, Conn. In such cases, biopsy device support block 53 is suitably modified to hold such devices.

Ultrasound transducer is connected to processing system 110 for generating and displaying on display 100 an ultrasound image that is orthogonal to the plane of lower compression plate 42. Ultrasound transducer 52 may comprise a single piston, annular or phased array imaging device of conventional design that preferably operates in a range of about 2 to 15 MHZ. More preferably, the ultrasound transducer produces a signal in the transmit mode of a 10 MHZ burst having a 100% bandwidth, and may be coupled to the underside of lower compression plate 42 using a suitable acoustic coupling.

When the biopsy device is pressed against the upper surface of the tissue, or inserted into the tissue, the biopsy needle will be visible in the ultrasound image displayed for the clinician's viewing on display 100. Accordingly, biopsy needle 54 may be guided to a selected region of the tissue under guidance of the ultrasound image generated by ultrasound transducer 52.

C-shaped support arm 49 provides additional advantages for use in imaging and biopsying tissue, as will now be described. Holder 51, ultrasound transducer 52 and biopsy device support block 53 are maintained in relative alignment along a plane substantially parallel to the patient's chest by C-shaped support arm 49. Thus, when slide block 50 is moved along guide arm 43, the clinician is able to obtain and display images of the tissue on display 100 to conduct a thorough examination.

In addition holder 51 and biopsy device support block 53 may be moved laterally along lower arm 49a and upper arm 49c, respectively, while still maintaining proximal and distal alignment of the needle or cannula of the biopsy device with the ultrasound image, i.e., both elements remain in the same plane relative to the chest wall. Further, the trajectory of the biopsy needle or cannula may be determined in the ultrasound image simply by contacting the needle or cannula to the tissue, thus allowing biopsy device support block 53 to be moved along upper arm 49c to position the biopsy device.

Referring now to FIGS. 4A and 4B, alternative biopsy system 60 is described, in which complete alignment of the ultrasound transducer and biopsy device support block is maintained. Biopsy system 60 includes rigid housing 61 including sonolplate 62, support baron plate 62, support bars 63, slide block 64, top block 65, and upper compression plate 66 arranged as described for biopsy system 40 of FIGS. 3. Support bars 63, upper compression plate 66, and lower compression plate 62 are configured as described with respect to FIGS. 2.

Guide arm 67 comprises an L-shaped member having first leg 67a disposed parallel to the lateral surface of housing 61 and second leg 67b slidably disposed in slot 68 in housing 61. Connector block 69 is slidably disposed on first leg 67a of guide arm 67 for movement towards and away from the patient's chest.

Connector block 69 carries transducer support arm 70 which in turn supports holder 71 in which ultrasound transducer 72 is disposed. Connector block 69 also provides a bore through which L-shaped support rod 73 is adjustably carried. Biopsy device support block 74 is disposed on an end of L-shaped support rod 73 for carrying a biopsy device, such as needle 75. As shown in FIG. 4B, biopsy device support block 74 holds the needle or cannula of the biopsy device so that it is aligned with the image field of ultrasound transducer 72.

Second leg 67b is supported within housing 61 by suitable elements so that second leg 67b may be moved in a plane parallel to the patient's chest to adjust the side to side positioning of ultrasound transducer 72 and biopsy device support block 71 while maintaining these components in alignment. In addition, L-shaped support rod 73 may be vertically adjusted relative to the upper compression plate to vary the height of the biopsy device support block above the patient's tissue.

Unlike the embodiment of FIGS. 3, the embodiment of FIGS. 4 maintains complete alignment of biopsy device support block 74 and ultrasound transducer 72, even during side-to-side movement of the scanner, by translating the entire arrangement in connection with movement of second leg 67b of guide arm 67.

Referring now to FIGS. 5A and 5B, another alternative biopsy system 80 is described, in which alignment of the ultrasound transducer and biopsy device support block is maintained partly by mechanical alignment and partly by electronic tracking. Biopsy system 80 includes rigid housing 81 including sonolucent lower compression plate 82, support bars 83, slide block 84, top block 85, and upper compression plate 86 arranged as described for biopsy system 40 of FIGS. 3. Support bars 83, upper compression plate 86, and lower compression plate 82 are configure as described with respect to FIG. 2.

Guide arm 87 is affixed to one or both sides of housing 81 (only one such guide is shown for clarity in FIG. 5A). Connector block 88 carries transducer support arm 89. Support arm 89 in turn supports holder 90 in which ultrasound transducer 91 is disposed. Connector block 88 also provides a bore through which support rod 92 is adjustably carried. Biopsy device support block 93 is disposed on an end of support rod 92 for carrying a biopsy device, such as needle 94.

As will be apparent from FIG. 5B, transducer support arm 89 aligns ultrasound transducer 91 with biopsy device support block 93 in a plane parallel to the patient's chest wall. In a preferred embodiment, support rod 92 has disposed within it a printed circuit board arrangement of parallel, spaced-apart copper strips and connector block 88 includes a linear encoder that senses the static capacitance of the copper strips as the encoder is manually slid through connector block 88.

Thus, as support rod 92 is moved through connector block 88, the linear encoder outputs a signal corresponding to its displacement from a preset reference point, preferably, the upper surface of lower compression plate 82. The signal output by linear encoder is provided to processing system 110 via connecting cable 95. The linear encoder preferably has a displacement accuracy of about plus/minus 0.05 mm, and is available from Sylvac S. A., Crissier, Switzerland, and distributed in the United States by Fowler Company, Inc., Chicago, Ill., as Part No. 54-050-000.

Biopsy system 80 of FIG. 5 provides partial alignment of the biopsy device support block 93 with ultrasound transducer 91 through the connection of transducer support arm 89 to connector block 88. Thus, the clinician is assured that the trajectory of the needle or cannula of the biopsy device will intercept the tissue displayed in the ultrasound image. In addition, the use of a linear encoder in conjunction with connector block 88 enables the vertical height of biopsy device to be determined and the needle or cannula trajectory to be displayed superimposed on the ultrasound image of the tissue on display 100, as described in the above-incorporated U.S. application Ser. No. 08/421,381.

It will be understood that the foregoing is merely illustrative of the apparatus and methods of the present invention, and that various modifications can be made by those skilled in the art without departing from the scope and spirit of the invention.

What is claimed is:

1. Apparatus for positioning a biopsy device having a needle or cannula for insertion into a tissue mass, the apparatus for use in a system including a display, the apparatus comprising:

a first compression plate having first and second surfaces, the tissue mass immobilized against the first surface;

a second compression surface adjacent the first compression plate and defining a compression area therebetween;

an ultrasound transducer disposed adjacent the first compression plate and acoustically coupled to the second surface of the first compression plate;

a biopsy device support block; and a connecting member for securing the biopsy device support block and the ultrasound transducer, wherein the connecting member maintains alignment of the ultrasound transducer to the biopsy device support block in at least one plane.

2. The apparatus as defined in claim 1 further comprising a biopsy device having a needle or cannula carried in the biopsy device support block, the ultrasound transducer generating an image of the tissue mass including a portion of needle or cannula, the image being displayed on the display.

3. The apparatus as defined in claim 1 wherein the connecting member comprises a C-shaped support arm including first and second legs, the ultrasound transducer is carried on the first leg and the biopsy device support block is carried on the second leg.

4. The apparatus as defined in claim 1 wherein the connecting member maintains alignment of the ultrasound transducer to the biopsy device support block in a second plane orthogonal to the at least one plane.

5. The apparatus as defined in claim 4 wherein the connecting member comprises a transducer support arm, a connector block and an L-shaped support rod, the ultrasound transducer is carried on a transducer support arm and the biopsy device support block is carried on the L-shaped support leg.

6. The apparatus as defined in claim 1, wherein the connecting member further includes a means for determining a vertical displacement of the biopsy device support block relative to the first surface of the first compression plate.

7. The apparatus as defined in claim 6 wherein the means for determining comprises at least one encoder.

8. The apparatus as defined in claim 1 wherein the ultrasound transducer provides real-time imaging of the tissue mass.

9. The apparatus as defined in claim 1 wherein the ultrasound transducer provides imaging of the needle or cannula of the biopsy device after the needle or cannula has been inserted into the tissue mass.

10. The apparatus as defined in claim 1 further comprising a means for moving the second compression surface toward the first compression plate, the means for moving arranged so that the second compression surface is displaced away from a patient's chest wall as the second compression surface moves toward the first compression plate.

11. The apparatus as defined in claim 10 wherein the second compression surface is inclined at an angle inward towards the patient's chest wall, relative to a plane orthogonal to the patient's chest wall.

12. The apparatus as defined in claim 10 wherein the first compression plate is inclined at an angle inward towards the patient's chest wall, relative to a plane orthogonal to the patient's chest wall.

13. The apparatus as defined in claim 10 wherein a first surface of the second compression surface has a surface that grips the tissue mass to prevent movement of the tissue mass from between the first surface of the first compression plate and the second compression surface when the tissue mass is disposed therebetween.

14. The apparatus as defined in claim 1 wherein the apparatus further comprises a second compression surface and means for moving the second compression surface relative to the first surface to compress the tissue mass therebetween.

15. The apparatus as defined in claim 14 wherein the second compression surface defines an aperture through which the needle or cannula of the biopsy device may be disposed.

16. The apparatus as defined in claim 14 wherein the first surface defines a first area and the second compression surface defines a second area, the second area being substantially smaller than the first area.

* * * * *